US010478120B2

(12) United States Patent
Walczak et al.

(10) Patent No.: US 10,478,120 B2
(45) Date of Patent: Nov. 19, 2019

(54) MRI-GUIDED INTRAARTERIAL CATHETER-BASED METHOD FOR PREDICTING TERRITORY OF LOCAL BLOOD BRAIN BARRIER OPENING

(71) Applicant: The Johns Hopkins University, Baltimore, MD (US)

(72) Inventors: Piotr Walczak, Fulton, MD (US); Monica Pearl, Baltimore, MD (US); Miroslaw Janowski, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/311,696

(22) PCT Filed: May 17, 2015

(86) PCT No.: PCT/US2015/031278
§ 371 (c)(1),
(2) Date: Nov. 16, 2016

(87) PCT Pub. No.: WO2015/179258
PCT Pub. Date: Nov. 26, 2015

(65) Prior Publication Data
US 2017/0079581 A1    Mar. 23, 2017

Related U.S. Application Data

(60) Provisional application No. 61/994,880, filed on May 17, 2014.

(51) Int. Cl.
*A61B 5/00* (2006.01)
*A61K 47/26* (2006.01)
(Continued)

(52) U.S. Cl.
CPC ............ *A61B 5/4839* (2013.01); *A61B 5/055* (2013.01); *A61K 9/0085* (2013.01);
(Continued)

(58) Field of Classification Search
CPC ........ A61B 5/4839; A61B 5/055; A61M 5/14; A61K 49/08; A61K 31/198; A61K 31/047;
(Continued)

(56) References Cited

U.S. PATENT DOCUMENTS

2002/0038086 A1    3/2002  Hynynen et al.
2002/0164289 A1*  11/2002  McMurry .......... A61K 49/0002
                                                            424/9.361
(Continued)

OTHER PUBLICATIONS

Hynynen, et al. "Noninvasive MR Imaging-guided Focal Opening of the Blood-Brain Barrier in Rabbits". Radiology. Sep. 2001, p. 640-646. (Year: 2001).*
(Continued)

*Primary Examiner* — Amber R Stiles
(74) *Attorney, Agent, or Firm* — Mintz Levin Cohn Ferris Glovsky and Popeo, P.C.; Peter F. Corless

(57) ABSTRACT

The present invention provides a method of administering a therapeutic agent directly to the brain parenchym through a compromised region of the blood-brain barrier in a subject having a brain disorder, that involves first disrupting the blood-brain barrier (BBB) at an isolated region by locally administering an effective amount of a hyperosmolar agent at said region using a catheter, followed by administering a therapeutically effective amount of a therapeutic agent. The step of disrupting the BBB is carried out with non-invasive MR (magnetic resonance) imaging with a contrast agent to visualize local parenchymal transcatheter perfusion at said isolated BBB region thereby indicating that the BBB region is compromised. The method of the invention allows for
(Continued)

highly precise drug delivery to the brain through blood brain barrier disruption at specifically controlled regions.

17 Claims, 6 Drawing Sheets

(51) Int. Cl.
*A61K 9/00* (2006.01)
*A61K 49/10* (2006.01)
*A61K 48/00* (2006.01)
*A61B 5/055* (2006.01)
*A61K 31/047* (2006.01)
*A61K 31/198* (2006.01)
*A61K 49/08* (2006.01)
*A61M 5/14* (2006.01)

(52) U.S. Cl.
CPC .......... *A61K 31/047* (2013.01); *A61K 31/198* (2013.01); *A61K 47/26* (2013.01); *A61K 48/0075* (2013.01); *A61K 49/08* (2013.01); *A61K 49/103* (2013.01); *A61M 5/14* (2013.01)

(58) Field of Classification Search
CPC .............. A61K 48/0075; A61K 49/103; A61K 9/0085; A61K 47/26
See application file for complete search history.

(56) References Cited

U.S. PATENT DOCUMENTS

| | | | |
|---|---|---|---|
| 2005/0169902 A1* | 8/2005 | Borlongan | A61K 9/0019 424/93.71 |
| 2006/0024359 A1* | 2/2006 | Walker | A61K 9/0009 424/450 |
| 2008/0183070 A1* | 7/2008 | Unal | A61B 5/055 600/414 |
| 2010/0172842 A1* | 7/2010 | Israeli | A61B 5/055 424/9.3 |
| 2011/0318431 A1* | 12/2011 | Gulati | A61K 9/0019 424/681 |
| 2013/0158387 A1 | 6/2013 | Tanttu | |

OTHER PUBLICATIONS

Roman-Goldstein, S.M. et al., "Effects of gadopentetate dimeglumine administration after osmotic blood-brain barrier disruption: toxicity and MR imaging findings". American Journal of Neuroradiology, 1991, vol. 12, pp. 885-890.

International Search Report issued in corresponding International Application No. PCT/US2015/031278, dated Nov. 27, 2015, 4 pages.

Written Opinion issued in corresponding International Application No. PCT/US2015/031278, dated Nov. 27, 2015, 6 pages.

* cited by examiner

MRI-GUIDED INTRAARTERIAL CATHETER-BASED METHOD FOR PREDICTING TERRITORY OF LOCAL BLOOD BRAIN BARRIER OPENING

CROSS-REFERENCE TO RELATED APPLICATIONS

The present invention is the U.S. national stage pursuant to 35 U.S.C. § 371, of International Application Ser. No. PCT/US2015/031278, filed May 17, 2015 and published in English on Nov. 26, 2015 as publication WO2015/179258 A2, which claims priority to, and the benefit under 35 U.S.C. § 119(e) of U.S. provisional patent application No. 61/994,880, entitled "MRI-Guided Intraarterial Catheter-Based Method for Predicting Territory of Local Blood Brain Barrier Opening," filed May 17, 2014. The entire contents of the aforementioned patent applications are incorporated herein by this reference.

FIELD

The invention generally relates to a novel method for enhancing selective drug delivery to the brain via the blood-brain barrier (BBB). In particular, the invention relates a reproducible and precise method to reversibly open the BBB involving intraarterial injection of a hyperosmolar agent combined with non-invasive MR imaging to accurately predict the territory of BBB opening.

BACKGROUND

The blood-brain barrier (BBB) is a highly selective permeability barrier that separates the circulating blood in the brain from the central nervous system and which functions to shield the brain from harmful elements in the blood and cerebrospinal fluid (CSF), while facilitating the exchange of essential amino acids, ions, metabolites, neurotransmitters, oxygen, carbon dioxide, growth factors, and other necessary nutrients and cellular wastes within the brain tissue. Although the BBB has evolved to effectively regulate brain homeostasis and to protect the brain from the harmful effects of unwanted elements in the blood and CSF, such as toxins and bacteria, the BBB also presents a significant challenge in the context of delivering therapeutic agents to the brain. Therapeutic molecules and antibodies that might otherwise be effective in diagnosis and therapy do not generally cross the BBB in adequate amounts to be effective in treatment. Overcoming the difficulty of delivering such therapeutics—ranging from small molecules, protein therapeutics and antibodies, and nucleic acids—presents a major challenge in the treatment of most brain disorders, including brain cancer and tumors, stroke, Alzheimer's disease, and dementia.

A variety of approaches have been explored to improve the efficacy of drug delivery to the brain such that effective treatments may be administered. Mechanisms for drug targeting in the brain involve going either "through" or "behind" the BBB. For example, methods for drug delivery through the BBB can involve biochemical means, i.e., by the use of vasoactive substances, such as bradykinin. Other modalities can include localized exposure to high-intensity focused ultrasound (HIFU). However, such an approach leaves a long-term opening and as such, leaves the brain vulnerable to infection and toxins. Still other methods may entail the use of endogenous transport systems, including carrier-mediated transporters, such as glucose and amino acid carriers or receptor-mediated transcytosis. In addition, modalities may include active blocking of efflux transporters. Methods may also include intracerebral implantations, such as with needles, and convection-enhanced distribution.

One well-known, yet problematic strategy to move desired drugs into the brain is to physically disrupt the BBB with hyperosmolar agents. The disruption to the BBB allows makes it possible for drugs or desired therapeutic agents to diffuse the brain parenchym through the compromised BBB. Osmotic disruption typically uses a concentrated dose of mannitol to remove fluid from the brain's endothelial cells, which causes them to shrink, thereby opening the tight endothelial cell junctions. The disadvantage in this approach is that BBB disruption also weakens the natural protective function of the BBB against bacterial infections and/or toxins. In addition, this approach sees highly results due in part to the high unpredictability and/or lack of control as to the particular the location and range of the BBB disruption that results from the hyperosmolar agent. This lack of predictability in knowing the territory of the BBB opening significantly limits the ability to achieve highly targeted intra-arterial drug administrations. Thus, despite its discovery over 40 years ago, hyperosmotic BBB opening (BBBO) remains highly variable, preventing its widespread implementation.

Accordingly, there is an unmet need for improved methods of intra-arterial drug administration in the brain that provides reproducible and highly selective delivery of drugs to the brain for treating a wide array of disorders, including cancer and neurodegenerative disorders.

SUMMARY

Until now BBB opening based on intraarterial injection of hyperosmolar agents has found only limited clinical applications and this was due to variability of results. We discovered that the area of BBB opening can be precisely determined and guided using non-invasive MR imaging. By using intraarterial catheter and injection of contrast agent we can show local parenchymal transcatheter perfusion. As contrast agent we have used iron oxide nanoparticle formulation (FDA-approved for treatment of anemia), which is isotonic and we found is safe for intraarterial injection. We have found that the transcatheter perfusion territory varies from subject to subject and this likely is the source of variability in BBB opening results. We demonstrated that the locality of catheter driven parenchymal flow can be precisely modulated by varying infusion rate and position of the catheter tip and that accurately defines brain area, in which the BBB will be open. Thus it allows for safe and temporary and spatially precise opening of BBB. The local parenchymal flow is different in subjects, thus for desired effect such titrating of injection rate must be performed for each case independently.

In certain aspects, the invention provides a technique that enables the prediction and optimization of the BBBO territory. It was found that the microcatheter tip position and the speed of hyperosmolar mannitol injection, both major determinants of the targeted territory, could be modulated in real-time as guided by trans-catheter perfusion MRI.

Accordingly, in one aspect, the present invention is directed to a method of administering a therapeutic agent directly to the brain parenchym through a compromised region of the blood-brain barrier in a subject having a brain disorder, comprising: (a) disrupting the blood-brain barrier (BBB) at an isolated region by locally administering an effective amount of a hyperosmolar agent at said region using a catheter, and (b) administering a therapeutically effective amount of a therapeutic agent, wherein said disrupting step is performed using non-invasive MR (magnetic resonance) imaging with a contrast agent to visualize local parenchymal transcatheter perfusion at said isolated BBB region thereby indicating that the BBB region is compromised.

In some embodiments, the brain disorder is a proliferative disorder. The brain disorder can also be a neurological disorder, such as brain damage, brain dysfunction, cranial nerve disorder, autonomic nervous system disorder, seizure disorder, movement disorder, sleep disorder, migraine, a central neuropathy, or a neuropsychiatric illness. In one particular embodiment, the disorder is Alzheimer's disease.

In certain embodiments, the therapeutic agent can be an agent for treating a proliferative disorder. The agent can be a small molecule pharmaceutical, a protein therapeutic, a therapeutic antibody, a therapeutic nucleic acid molecule, or a composition comprising any of same.

In certain other embodiments, the effective amount of the hyperosmolar agent refers to the administration at an effective rate and/or for an effective period of time. The hyperosmolar agent can be, for example, mannitol, glycerin, isosorbide, or urea.

In some embodiments, the isolated region of the BBB is associated with the basilar artery (i.e., associated with the endothelial cell-coated capillaries that are connected to this arterial region). The region of the BBB targeted for local disruption can also include other cranial arteries, including the vertebral artery, the occipital artery, the basilar artery, the superficial temporal artery, the middle cerebral artery, the anterior cerebral artery, the ophthalmic artery, and the internal carotid artery.

In some other embodiments, the contrast agent used to visual local parenchymal transcatheter perfusion is gadolinium and/or Feraheme or a combination thereof. The contrast agent can also be selected from the group consisting of: gadoterate (Dotarem); gadodiamide (Omniscan); gadobenate (MultiHance); gadopentetate (Magnevist, Magnegita, Gado-MRT ratiopharm); gadoteridol (ProHance); gadoversetamide (OptiMARK); gadoxetate (Primovist); gadobutrol (Gadovist); gadoterate (Dotarem); gadodiamide (Omniscan); gadobenate (MultiHance); gadopentetate (Magnevist); gadoteridol (ProHance); gadofosveset (Ablavar, formerly Vasovist); gadoversetamide (OptiMARK); gadoxetate (Eovist); and gadobutrol (Gadavist).

In still other embodiments, the hyperosmolar agent is mannitol. The hyperosmolar agent can also be glycerin, isosorbide, or urea. In yet other embodiments, the hyperosmolar agent is administered at a pre-determined optimized infusion rate, which can be determined on a subject-by-subject basis to optimize the delivery of agents through the BBB.

In another aspect, the present invention provides a computer-implemented system for measuring, monitoring, processing, and calculating a model for optimized BBB opening in a subject undergoing BBB hyperosmolar-based perfusion during real-time MRI imaging. The computer-implemented comprises a processor that processes calculates a model for optimized BBB opening in a subject that is based on user-defined input data (e.g., perfusion flow rate, hyperosmolar agent concentration, perfusion time, catheter tip position, patient data (e.g., age, family history, medical record, etc.) together with MRI based visual input data (e.g., measurements of the size or extent of brain parenchymal flow and/or BBB opening measurements taken in real-time during perfusion). Additional data, such as the level or concentration of a marker agent (e.g., fluorescent compound, drug analog) that has crossed the open BBB region, may also be provided to the processing device. The processing devices receives the user input data and the MRI-based data and processes same via a suitable algorithm or software and calculates a model that predicts the optimal conditions for BBB opening in the subject. The processed information and/or model may be stored in a storage device or a database.

In a further aspect, the present invention relates to the use of the predictive models of the invention to predict the optimal conditions for BBB opening that may be used on a new subject without having to first establish optimal BBB conditions in said patient, i.e., avoid having to empirically test multiple sets of conditions to identify the most suitable BBB formation conditions.

In certain embodiments, the invention also relates to any and all necessary catheter-related control equipment, pumps, drive systems, electrical and fluid control systems, as well as other separate or integrated systems for measuring and visualizing the method of the invention, e.g., fluoroscopic or other visualization systems, vital sign monitoring systems, and the like.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION

Figure 1:
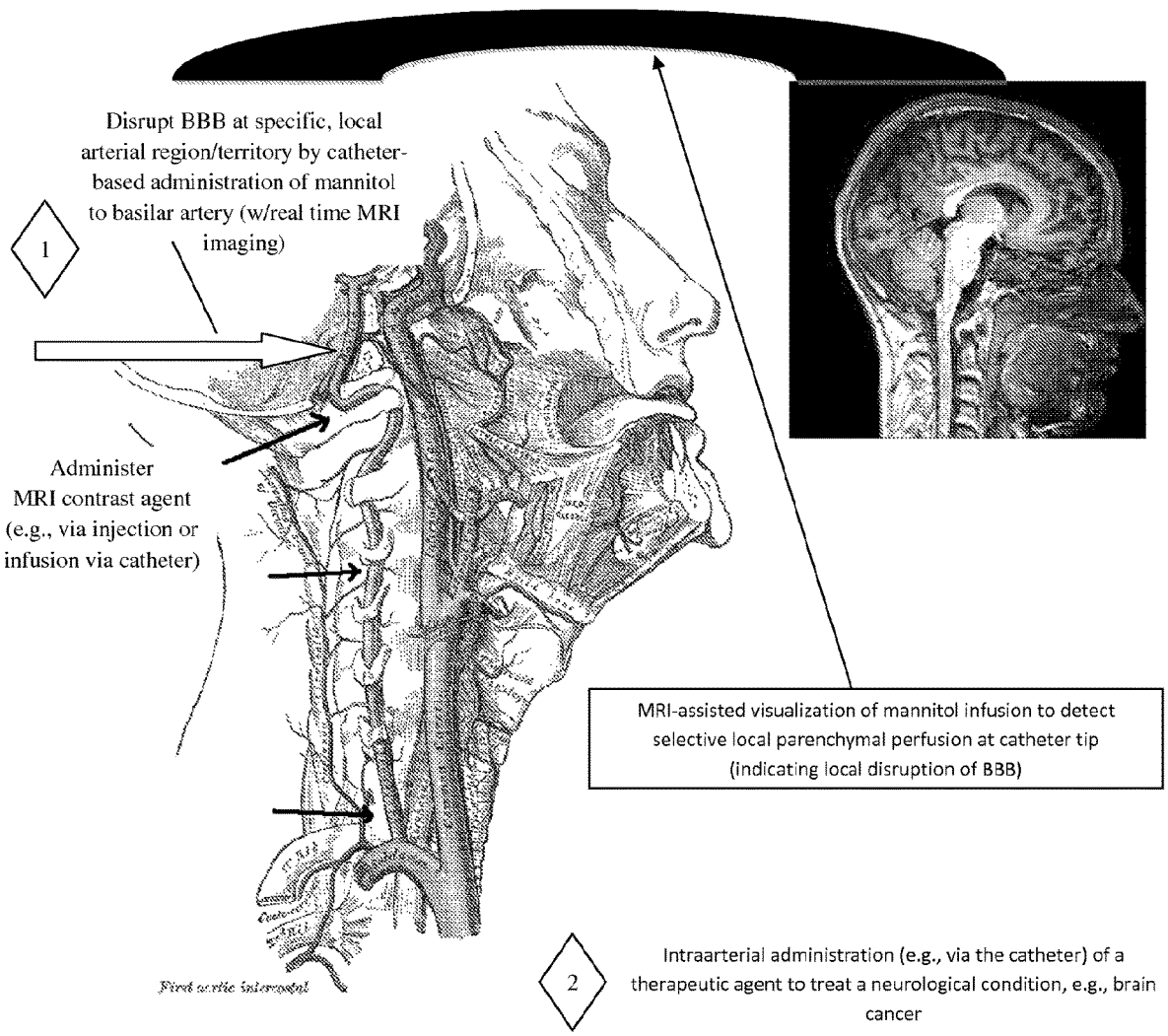
FIG. 1. Provides a schematic depicting an embodiment of the method of the invention.

It will be appreciated that blood-brain barrier (BBB) opening based on intraarterial injection of hyperosmolar agents, e.g., mannitol, has to date found only limited clinical applications. The limited use of this approach was due to significant variability in results. The present inventors have discovered that the area of BBB opening can be precisely determined and guided using non-invasive magnetic resonance (MR) imaging. The method of the invention in one aspect involves introducing an MR contrast agent, e.g., iron oxide nanoparticles, by intraarterial catheter-based injection and imaging local parenchymal transcatheter perfusion. The inventors surprisingly found that the local transcatheter perfusion territory varies from subject to subject and is likely the source and/or cause of variability in BBB opening results. The inventors for the first time demonstrated that the locality of catheter driven parenchymal flow can be precisely modulated by varying infusion rate and position of the catheter tip, which accurately defines the brain area in which the BBB will be open. Thus it allows for safe, temporary, and spatially precise opening of the BBB. The local parenchymal flow may be different among subjects; thus, for desired effect such titrating of injection rate can be performed on a subject-by-subject basis. Once a BBB opening has been identified and its position is known, a therapeutic agent may be administered to the brain in a highly selective and local manner. In addition, the invention provides a computer-implemented system for measuring, monitoring, processing, and calculating a model for optimized BBB opening in a subject undergoing BBB hyperosmolar-based perfusion during real-time MRI imaging.

In a further aspect, the present invention relates to the use of the predictive models of the invention to predict the optimal conditions for BBB opening that may be used on a new subject without having to first establish optimal BBB conditions in said patient, i.e., avoid having to empirically test multiple sets of conditions to identify the most suitable BBB formation conditions.

In certain embodiments, the invention also relates to any and all necessary catheter-related control equipment, pumps, drive systems, electrical and fluid control systems, as well as other separate or integrated systems for measuring and visualizing the method of the invention, e.g., fluoroscopic or other visualization systems, vital sign monitoring systems, and the like.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Definitions

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

Prior to now, the BBB opening by hyperosmolar contrast agents was performed without image guidance and results were variable and unreliable. The method of the invention is based on intraarterial injection of hyperosmolar agent preceded by MRI contrast injection, which allows for precise and reproducible opening of BBB.

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the singular forms "a", "and", and "the" include plural references unless the context clearly dictates otherwise. All technical and scientific terms used herein have the same meaning.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. Certain characteristic signs, symptoms, and related factors can be quantitated through a variety of methods to yield important diagnostic information. As used herein the disorder, disease, or abnormal state can be a cancer of the brain or a benign or malignant brain tumor. The disorder, disease, or abnormal state can also be a neurological disorder. As used herein, a neurological disorder is any disorder of the body's nervous system. Structural, biochemical or electrical abnormalities in the brain, spinal cord or other nerves can result in a range of symptoms. Examples of symptoms include paralysis, muscle weakness, poor coordination, loss of sensation, seizures, confusion, pain and altered levels of consciousness. There are many recognized neurological disorders, some relatively common, but many rare. They may be assessed by neurological examination, and studied and treated within the specialties of neurology and clinical neuropsychology. The term neurological disorder may also refer to any cancer arising from or within a neurological tissue, including brain cancer or tumors.

Neurological disorders can be categorized according to the primary location affected, the primary type of dysfunction involved, or the primary type of cause. The broadest division is between central nervous system (CNS) disorders and peripheral nervous system (PNS) disorders. The Merck Manual lists brain, spinal cord and nerve disorders in the following overlapping categories, all of which are contemplated by the invention:

Brain damage according to cerebral lobe, i.e., Frontal lobe damage, Parietal lobe damage, Temporal lobe damage, and Occipital lobe damage;

Brain dysfunction according to type: Aphasia (language), Dysarthria (speech), Apraxia (patterns or sequences of movements), Agnosia (identifying things/people), and Amnesia (memory);

Spinal cord disorders;

Peripheral neuropathy & other peripheral nervous system disorders;

Cranial nerve disorders such as Trigeminal neuralgia;

Autonomic nervous system disorders, such as dysautonomia and Multiple System Atrophy;

Seizure disorders, such as epilepsy;

Movement disorders of the central & peripheral nervous system, such as Parkinson's disease, essential tremor, amyotrophic lateral sclerosis (ALS), Tourette's Syndrome, multiple sclerosis & various types of peripheral neuropathy;

Sleep disorders, such as narcolepsy;

Migraines and other types of headache, such as cluster headache and tension headache;

Lower back and neck pain;

Central Neuropathy (see Neuropathic pain); and

Neuropsychiatric illnesses (diseases and/or disorders with psychiatric features associated with known nervous system injury, underdevelopment, biochemical, anatomical, or electrical malfunction, and/or disease pathology e.g., Attention deficit hyperactivity disorder, Autism, Tourette's Syndrome & some cases of Obsessive compulsive disorder as well as the neurobehavioral associated symptoms of degeneratives of the nervous system such as Parkinson's disease, Essential tremor, Huntington's disease, Alzheimer's disease, Multiple sclerosis & organic psychosis.)

As used herein, the term "obtaining" is understood herein as manufacturing, purchasing, or otherwise coming into possession of.

As used herein, "one or more" is understood as each value 1, 2, 3, 4, 5, 6, 7, 8, 9, 10, and any value greater than 10.

The term "or" is used inclusively herein to mean, and is used interchangeably with, the term "and/or," unless context clearly indicates otherwise. For example, as used herein, filamin B or LY9 is understood to include filamin B alone, LY9 alone, and the combination of filamin B and LY9.

As used herein, "patient" or "subject" can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient.

The term "therapeutic effect" refers to a local or systemic effect in animals, particularly mammals, and more particularly humans caused by a pharmacologically active substance. The term thus means any substance intended for use in the diagnosis, cure, mitigation, treatment, or prevention of disease, or in the enhancement of desirable physical or mental development and conditions in an animal or human. A therapeutic effect can be understood as a decrease in tumor growth, decrease in tumor growth rate, stabilization or decrease in tumor burden, stabilization or reduction in tumor size, stabilization or decrease in tumor malignancy, increase in tumor apoptosis, and/or a decrease in tumor angiogenesis.

As used herein, "therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment, e.g., is sufficient to ameliorate at least one sign or symptom of the disease, e.g., to prevent progression of the disease or condition, e.g., prevent tumor growth, decrease tumor size, induce tumor cell apoptosis, reduce tumor angiogenesis, prevent metastasis. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

As used herein, "treatment," particularly "active treatment," refers to performing an intervention to treat prostate cancer in a subject, e.g., reduce at least one of the growth rate, reduction of tumor burden, reduce or maintain the tumor size, or the malignancy (e.g., likelihood of metastasis) of the tumor; or to increase apoptosis in the tumor by one or more of administration of a therapeutic agent, e.g., chemotherapy or hormone therapy; administration of radiation therapy (e.g., pellet implantation, brachytherapy), or surgical resection of the tumor, or any combination thereof appropriate for treatment of the subject based on grade and stage of the tumor and other routine considerations. Active treatment is distinguished from "watchful waiting" (i.e., not active treatment) in which the subject and tumor are monitored, but no interventions are performed to affect the tumor.

Watchful waiting can include administration of agents that alter effects caused by the tumor (e.g., incontinence, erectile dysfunction) that are not administered to alter the growth or pathology of the tumor itself.

As used herein, "MRI contrast agents" are a group of contrast media used to improve the visibility of internal body structures in magnetic resonance imaging (MRI). The most commonly used compounds for contrast enhancement are gadolinium-based. MRI contrast agents alter the relaxation times of atoms within body tissues where they are present after oral or intravenous administration. In MRI scanners, sections of the body are exposed to a very strong magnetic field, then a radiofrequency pulse is applied causing some atoms (including those in contrast agents) to spin and then relax after the pulse stops. This relaxation emits energy which is detected by the scanner and is mathematically converted into an image. The MRI image can be weighted in different ways giving a higher or lower signal.

As used herein, the "brain" or "brain parenchym" refers to the brain and brain stem tissues and any anatomic feature therein, and can include any anatomical region of the brain, such as the cerebrum (composed of the cortex and the corpus callosum), the diencephalon (composed of the thalamus, pineal body, and the hypothalamus), the brain stem (composed of the midbrain, pons, medulla oblongata), and the cerebellum. The brain or brain parenchym can also include any functional region of the brain, including the frontal lobe, temporal lobe, central sulcus, parietal lobe, and occipital lobe, as well as deep structures of the limbic system, including the limbic lobe, corpus callosum, mammillary body, olfactory bulb, septal nuclei, amygdala, hippocampus, cingulate gyrus, fornix, and thalamus. The term "brain parenchym" particularly refers to the functional portion of the brain, as compared to features that are merely structural.

As used herein, the term "compromised," as in a compromised blood-brain barrier (BBB) refers to a BBB which has been partially, but reversibly disrupted. The term particularly refers to where the tight junctions between capillary endothelial cells of the BBB have been compromised such that molecules and components of the blood and CFS may pass or diffuse into the brain parenchym through the compromised tight junctions.

As used herein, the "blood-brain barrier" (BBB) refers to a highly selective permeability barrier that separates the circulating blood from the brain extracellular fluid (BECF) in the central nervous system (CNS). The blood-brain barrier is formed by capillary endothelial cells, which are connected by tight junctions with an extremely high electrical resistance of at least 0.1 Ωm. The blood-brain barrier allows the passage of water, some gases, and lipid soluble molecules by passive diffusion, as well as the selective transport of molecules such as glucose and amino acids that are crucial to neural function. On the other hand, the blood-brain barrier may prevent the entry of lipophilic, potential neurotoxins by way of an active transport mechanism mediated by P-glycoprotein. Astrocytes are necessary to create the blood-brain barrier. A small number of regions in the brain, including the circumventricular organs (CVOs), do not have a blood-brain barrier. The blood-brain barrier occurs along all capillaries associated with cranial arteries and consists of tight junctions around the capillaries that do not exist in normal circulation. Endothelial cells restrict the diffusion of microscopic objects (e.g., bacteria) and large or hydrophilic molecules into the cerebrospinal fluid (CSF), while allowing diffusion of small hydrophobic molecules. Cells of the barrier actively transport metabolic products such as glucose across the barrier with specific proteins. This barrier also includes a thick basement membrane and astrocytic endfeet.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

In one aspect, the present invention is directed to a method of administering a therapeutic agent directly to the brain parenchym through a compromised region of the blood-brain barrier in a subject having a brain disorder, comprising: (1) disrupting the blood-brain barrier (BBB) at an isolated region by locally administering an effective amount of a hyperosmolar agent at said region using a catheter, (2) administering a therapeutically effective amount of a therapeutic agent, wherein said disrupting step is performed using non-invasive MR (magnetic resonance) imaging with a contrast agent to visualize local parenchymal transcatheter perfusion at said isolated BBB region thereby indicating that the BBB region is compromised. FIG. 1 generally depicts this aspect of the present invention.

In this embodiment, the first general step of the claimed method is to disrupt the BBB at a specific, local arterial region/territory by catheter-based administration of a hyperosmolar agent (e.g., mannitol) while using real-time MRI to visualize the detection of selective local parenchymal perfusion at the catheter tip, which shall indicate local disruption of the BBB (aka focal BBB disruption or BBBD). Once the BBBD has been detected, a therapeutic agent may be administered by intraarterial infusion, e.g., through the same or separate catheter, at the site or proximal the site of BBBD.

Prior to the present invention, BBB opening (aka reversible disruption) by hyperosmolar contrast agents (e.g., mannitol) was performed without image guidance and results were highly variable and unreliable. The present invention, as exemplified in the embodiment herein, is based on intraarterial injection or infusion of a hyperosmolar agent in combination with (e.g., before, after, about the same time) an MRI contrast agent that allows for detection of local or focal BBB disruption at or near the tip of the catheter. This then allows for a precise delivery of a therapeutic agent by intraarterial infusion to a specific location of BBBD, which in turn, greatly enhances the efficacy and effectiveness of delivery desired therapeutic agents to the brain parenchyma for improved or enhanced treatment of brain disorders and/or cancer.

In a particular embodiment, the infusion rate or injection rate of the hyperosmolar agent (e.g. mannitol) may be optimized prior to delivering a therapeutic agent in order to determine the optimized degree or level of selective perfusion of the brain parenchym, i.e., which in turn reflects the degree of the BBBD or opening of the BBB. Exemplary rates of perfusion can include any suitable perfusion rate, such as, 0.01 ml/sec. The infusion rate can also include any range from about 0.001 ml/sec, to about 0.005 ml/sec, to about 0.01 ml/sec, to about 0.015 ml/sec, to about 0.02 ml/sec, to about 0.025 ml/sec, to about 0.03 ml/sec, to about 0.035 ml/sec, to about 0.04 ml/sec, to about 0.045 ml/sec, to about 0.05 ml/sec, to about 0.06 ml/sec, to about 0.07 ml/sec, to about 0.08 ml/sec, to about 0.09 ml/sec, to about 0.10 ml/sec, to about 0.20 ml/sec, to about 0.30 ml/sec, to about 0.40 ml/sec, to about 0.50 ml/sec, to about 0.60 ml/sec, to about 0.70 ml/sec, to about 0.80 ml/sec, to about 0.90 ml/sec, or more. In addition, the length of time of perfusion may be adjusted such that the degree of perfusion of the brain parenchym is optimized, and in turn, the degree of opening of the BBB. For example, perfusion may continuously or discontinuously operate for about 0.1 sec, about 0.2 sec, about 0.3 sec, about 0.4 sec, about 0.5 sec, about 0.6 sec, about 0.7 sec, about 0.8 sec, about 0.9 sec, about 1.0 sec, about 1-1.5 sec, to about 1.25-1.75 sec, to about 1.5-2.0 sec, to about 1.75-3.0 sec, to about 2.0-10.0 sec, to about 5.0-30.0 sec, to about 10.0-50.0 sec, to about 20.0-60.0 sec, to about 1-2 min, to about 2-5 min to about 5-10 min, to about 9-25 min, to about 24-50 min, to about 49-150 min, to up to several hours or more. When optimizing the degree of BBB opening, one of ordinary skill in the art may also take into account the other physical properties of the desired therapeutic agent to be delivered across the BBBD, including, for example, the molecular weight or size of the agent, the degree of lipophilicity of the agent, the presence of charge, and the concentration of the agent as delivered, and any other similar physical properties.

In still other embodiments, the placement of the tip of the perfusion catheter in the cranial artery (e.g. in the Basilar artery) may be adjusted and/or moved within the artery during MRI visualization to optimize the perfusion into the brain parenchymal, and thus, in turn, optimize the opening of the BBB. As discovered by the inventors, as opening of the BBB varies from subject to subject, it is preferable to optimize the opening of the BBB for each subject desired to be treated by the methods of the invention.

Another aspect of the invention relates to a method of determining and/or measuring an optimized territory of blood-brain barrier (BBB) opening based on catheter perfusion of the BBB or select region thereof concomitant with non-invasive MR imaging to monitor local brain parenchymal transcatheter perfusion, thereby determining an optimized BBB opening. The inventors have discovered that transcatheter perfusion territory varies from subject to subject and this likely is the source of variability in BBB opening results known prior to the invention. The inventors discovered that the locality of catheter driven parenchymal flow can be precisely modulated by varying infusion rate and position of the catheter tip, which accurately defines the brain area in which the BBB will be open. The invention, thus, allows for safe and temporary and spatially precise opening of the BBB. The local parenchymal flow is different in subjects, thus for desired effect, the titrating of the injection rate preferably can be performed for each subject independently.

In another aspect, the present invention provides a computer-implemented system for measuring, monitoring, processing, and calculating a model for optimized BBB opening in a subject undergoing BBB hyperosmoral-based perfusion during real-time MRI imaging. The computer-implemented comprises a processor that processes calculates a model for optimized BBB opening in a subject that is based on user-defined input data (e.g., perfusion flow rate, hyperosmolar agent concentration, perfusion time, catheter tip position, patient data (e.g., age, family history, medical record, etc.) together with MRI based visual input data (e.g., measurements of the size or extent of brain parenchymal flow and/or BBB opening measurements taken in real-time during perfusion). Additional data, such as the level or concentration of a marker agent (e.g., fluorescent compound, drug analog) that has crossed the open BBB region, may also be provided to the processing device. The processing devices receives the user input data and the MRI-based data and processes same via a suitable algorithm or software and calculates a model that predicts the optimal conditions for BBB opening in the subject. The processed information and/or model may be stored in a storage device or a database.

In a further aspect, the present invention relates to the use of the predictive models of the invention to predict the optimal conditions for BBB opening that may be used on a new subject without having to first establish optimal BBB conditions in said patient, i.e., avoid having to empirically test multiple sets of conditions to identify the most suitable BBB formation conditions.

Opening of the Blood Brain Barrier (BBBO)

The blood brain barrier (BBB) is a dynamic system that regulates transport of materials between the blood, brain, and cerebrospinal fluid. An intact BBB effectually prevents passage of ionized water-soluble compounds with molecular weights exceeding 180 daltons (1) and is a major obstacle for drug delivery to the central nervous system (CNS), partly because most agents have molecular weights between 200 and 1200 Daltons (2). Interventional neuroradiology techniques are minimally invasive and allow for superselective delivery of therapeutic agents to specific CNS targets (3). In the presence of an intact BBB, safe, effective, and most importantly predictable BBBO is an important element to increase therapeutic efficacy for multiple CNS pathologies, including tumors and neurodegenerative disorders (4). Osmotic BBBO is a proven method that results in increased BBB permeability; however, this technique remains controversial due to its variability and the lack of non-invasive methods for real-time intra-procedural validation. Fluoroscopic x-ray-based digital subtraction angiography (DSA) is the current "gold standard" technique for catheter-based neurointerventions. Methods for assessing BBBO are currently not available with this modality; however, contrast-enhanced MRI is excellent for that purpose and lacks the exposure to ionizing radiation inherent with DSA. The objectives of the current experiments set forth herein were to develop a reproducible, predictable method of BBBO based on intra-arterial (IA) delivery while utilizing the optimal features offered by both modalities. As detailed elsewhere herein, the method was tested in New Zealand white rabbits, which were sufficiently large to enable a transfemoral approach and selective microcatheter access, and used a combination of fluoroscopic and advanced MRI techniques such as dynamic susceptibility contrast (DSC) MRI5 to guide intervention. Although the proposed method was tailored to the goal of treating incurable, surgically inoperable tumors such as diffuse intrinsic pontine gliomas (NCT01688401), its applications are broader than simply these aspects, as the method(s) allows for predictable, selective delivery for any therapeutic agent to the CNS.

Therapeutic agent delivery to the CNS is markedly impaired by an intact BBB, further diminishing the curative options for primary and metastatic tumors (6). Although osmotic BBBO was introduced over 40 years ago (7), its variability and lack of techniques for noninvasive validation in real-time during the procedure have limited its utility and currently only a few trials have implemented this strategy (8,9). Alternative new methods to overcome this barrier are currently being developed and include convection-enhanced delivery (10). However, drawbacks of this technique include peri-tumoral leakage (11) and the need for burr-hole placement. MRI guided high-intensity focused ultrasound (HIFU) is another strategy that utilizes acoustic ultrasound to induce mechanical stress and endothelial cell deformation to temporarily disrupt tight junctions, thereby increasing BBB permeability. Advantages are precise anatomic visualization and the ability to continuously monitor the tissue effect; however, the increased permeability window is narrow, which affects the scale and distribution of therapeutic molecule delivery into brain (12). In addition, the requirement for catheter placement for delivery of therapeutic agents makes it more practical and feasible to use the same targeting approach for localized BBBO using transcatheter injection of hyperosmotic agent rather than HIFU.

Treatable Disorders

The method of the invention may be used to treat any number of neurological disorders, including cancer of the brain.

Diseases can include neurological disorders, which can be categorized according to the primary location affected, the primary type of dysfunction involved, or the primary type of cause. The broadest division is between central nervous system (CNS) disorders and peripheral nervous system (PNS) disorders. The Merck Manual lists brain, spinal cord and nerve disorders in the following overlapping categories, all of which are contemplated by the invention:

Brain damage according to cerebral lobe, i.e., Frontal lobe damage, Parietal lobe damage, Temporal lobe damage, and Occipital lobe damage; Brain dysfunction according to type: Aphasia (language), Dysarthria (speech), Apraxia (patterns or sequences of movements), Agnosia (identifying things/people), and Amnesia (memory); Spinal cord disorders; Peripheral neuropathy & other peripheral nervous system disorders; Cranial nerve disorders such as Trigeminal neuralgia; Autonomic nervous system disorders, such as dysautonomia and Multiple System Atrophy; Seizure disorders, such as epilepsy; Movement disorders of the central & peripheral nervous system, such as Parkinson's disease, essential tremor, amyotrophic lateral sclerosis (ALS), Tourette's Syndrome, multiple sclerosis & various types of peripheral neuropathy; Sleep disorders, such as narcolepsy; Migraines and other types of headache, such as cluster headache and tension headache; Lower back and neck pain; Central Neuropathy (see Neuropathic pain); and Neuropsychiatric illnesses (diseases and/or disorders with psychiatric features associated with known nervous system injury, underdevelopment, biochemical, anatomical, or electrical malfunction, and/or disease pathology e.g., Attention deficit hyperactivity disorder, Autism, Tourette's Syndrome & some cases of Obsessive compulsive disorder as well as the neurobehavioral associated symptoms of degeneratives of the nervous system such as Parkinson's disease, Essential tremor, Huntington's disease, Alzheimer's disease, Multiple sclerosis & organic psychosis.)

Treatable diseases can also include brain tumors. Brain tumors are abnormal growths of new and unnecessary cells in or on the brain. It is thought that tumors occur when genetic factors or environmental damage impair normal cells so that they multiply and divide rapidly. There are many different kinds of brain tumors, which are classified in different ways depending on where the tumor originates, how quickly the tumor grows, and how destructive the tumor is.

Brain tumors are usually classified as either benign or malignant. Benign tumors tend to be slow-growing clusters of cells that rarely spread. Tumors are classified as malignant when they grow aggressively, invade other parts of the body, cause damage to critical functions, or are life threatening. Malignant tumors are also known as cancerous. Brain tumors that originate in the brain itself are called primary tumors. Primary brain tumors can start in the brain tissue, the brain lining (meninges), the skull, the nerves, or the pituitary gland. Tumors that originate somewhere else in the body and move into the brain are called metastatic tumors. Metastatic tumors are always malignant, since by definition they have invaded the brain from another part of the body. Very few primary brain tumors are benign, and even these tumors sometimes become malignant.

The invention contemplates treatment of all types and categories of brain tumors (whether cancerous or benign). Tumors can be optionally graded to indicate their degree of malignancy using a system developed by the World Health Organization (WHO). This system classifies tumors into four groups (WHO Grade I through IV) depending on factors such as how abnormal the cells are, how quickly the tumor is growing, the potential for invasion or spread of the tumor, and the blood supply of the tumor. Grade I tumors are considered benign and usually have very good survival rates. Grade II tumors are slow growing, but sometimes invade nearby tissue and/or recur after treatment. Grade III tumors have more abnormal cells and grow faster than Grade II tumors. Grade IV tumors are the most malignant. They grow rapidly and spread widely.

The invention contemplates treating any type of brain tumor, which can include the following types of benign brain tumors.

Meningiomas

A meningioma is a tumor that develops from the lining of the brain and spinal cord. It is the most common benign brain tumor in adults. A few meningiomas are malignant. The cause of meningiomas is unknown; however, some meningiomas are associated with specific genetic disorders, such as neurofibromatosis. Symptoms include seizure, headaches and loss of brain function (sensory problems, loss of coordination, etc.). Meningiomas usually grow slowly and may be treated at first with observation over time. For large meningiomas, surgery is usually the preferred treatment.

Acoustic Neuromas

Acoustic neuromas (a.k.a. vestibular schwannomas) are tumors arising from a cranial nerve. The tumor is usually benign and slow growing. The most common symptoms are hearing loss, ringing in the ears, vertigo (dizziness), and headaches. Options for treatment include observation, radiosurgery, and surgical resection. The ideal treatment in most cases is complete microsurgical tumor resection.

Pituitary Tumors

Pituitary tumors are tumors of the pituitary gland, which produces hormones to regulate the other glands in the body. These tumors may or may not secrete hormones. Often symptoms develop based on the type of hormone secreted. Some pituitary tumors are treated with medication alone, other with surgery, some with radiation, and some with a combination of all three treatments. Pituitary tumors represent approximately 10-15% of all brain tumors. They are most common in the third and fourth decade of life, and males and females are equally affected.

Colloid Cysts

Colloid cysts are benign tumors that only occur in the third ventricle, an area involved with cerebrospinal fluid flow. Tumors in this area can be life threatening by blocking the flow of cerebrospinal fluid, causing a condition called hydrocephalus. Hydrocephalus may cause headaches, nausea, vomiting, and even comas, which can lead to death. If the tumor is large enough, most neurosurgeons will treat the condition with surgical removal. Sometimes a ventricular shunt (a tube from the ventricles) is needed, which diverts and drains the cerebrospinal fluid and relieves pressure.

Arachnoid Cysts

An arachnoid cyst is a sac of cerebrospinal fluid that develops in the brain. Some of these cysts may develop in infancy, but often they are undiagnosed until a head injury occurs. Arachnoid cysts may cause no symptoms for a long time until they are large enough to put pressure on the brain or cause a deformity. Sometimes surgery is needed to create space around the cyst. Other cysts can be treated with a shunt.

Craniopharyngiomas

Craniopharyngiomas are benign tumors located above and behind the pituitary gland. These tumors grow slowly, but can cause vision problems or pituitary dysfunction. There is debate on how these tumors should be treated. Many neurosurgeons advocate surgical removal followed by radiation. In some cases, draining the cyst fluid may control the symptoms and halt growth.

Choroid Plexus Papillomas

Choroid plexus papillomas are benign tumors that occur in the brain's ventricular system from the cells that make spinal fluid. Treatment is usually surgical removal.

Hemangioblastomas

Hemangioblastomas are benign tumors of blood vessels that are often associated with cysts. They are usually treated with surgical removal, with or without radiation therapy.

Epidermoid and Dermoid Tumors

Epidermoid and dermoid tumors are benign tumors containing accumulated left over skin tissue within the head or spinal canal. The tumors usually require surgical removal.

The invention contemplates treating any type of brain tumor, which can include the following types of malignant brain tumors.

Primary Malignant Brain Tumors

The majority of primary brain tumors are malignant. Most primary malignant brain tumors arise from glial cells, which are tissues of the brain other than nerve cells or blood vessels. Unfortunately, these tumors can grow quickly and be very destructive. Management of these tumors depends primarily on the health of the patient and the location of the tumor. When feasible, treatment typically includes surgical removal followed by radiation and/or chemotherapy.

Metastatic Brain Tumors

These types of tumors originate in tissues outside of the brain, followed by metastasis to the brain. Metastatic tumors account for 10-15% of all brain tumors. The most common tumors that spread to the brain are those that originate in the lung, the breast, the kidney, or melanomas (skin cancer).

The method of the invention contemplates the treatment of any type of brain tumor by administration of therapeutically effective amounts of anti-cancer or anti-proliferative disorder agents. Such agents can include small molecule therapeutics, therapeutic peptides, therapeutic antibodies, and therapeutic nucleic acid molecules.

Therapeutic Agents

The method of the invention contemplates the administration of any suitable therapeutic agent capable of treating a neurological disorder, including brain cancer.

Therapeutic agents can include any neurologically active agents acting at synaptic and neuroeffector junction sites. The neurologically active agent useful in the present invention may be one that acts at the synaptic and neuroeffector junctional sites; such as a cholinergic agonist, a anticholinesterase agent, catecholamine and other sympathomimetic drugs, an adrenergic receptor antagonist, an antimuscarinic drug, and an agent that act at the neuromuscular junction and autonomic ganglia.

Examples of suitable cholinergic agonists include, but are not limited to, choline chloride, acetylcholine chloride, methacholine chloride, carbachol chloride, bethanechol chloride, pilocarpine, muscarine, arecoline and the like. See Taylor, P., in The Pharmacological Basis of Therapeutics, Gilman, et al., eds., Pergamon Press, New York, 1990, 8th edition, Chapter 6, pp. 122-130.

Suitable anticholinesterase agents are exemplified by the group consisting of carbaril, physostigmine, neostigmine, edrophonium, pyridostigmine, demecarium, ambenonium, tetrahydroacridine and the like. See Taylor, P., in The Pharmacological Basis of Therapeutics, Gilman, et al., eds., Pergamon Press, New York, 1990, 8th edition, Chapter 7, pp. 131-149.

Suitable catecholamines and sympathomimetic drugs include the subclasses of endogenous catecholamines, beta-adrenergic agonists, alpha-adrenergic agonists and other miscellaneous adrenergic agonists.

Within the subclass of endogenous catecholamines, suitable examples include epinephrine, norepinephrine, dopamine and the like. Suitable examples within the subclass of beta-adrenergic agonists include, but are not limited to, isoproterenol, dobutamine, metaproterenol, terbutaline, albuterol, isoetharine, pirbuterol, bitolterol, ritodrine and the like. The subclass of .alpha.-adrenergic agonists can be exemplified by methoxamine, phenylephrine, mephentermine, metaraminol, clonidine, guanfacine, guanabenz, methyldopa and the like. Other miscellaneous adrenergic agents include, but are not limited to, amphetamine, methamphetamine, methylphenidate, pemoline, ephedrine and ethylnorepinephrine and the like. See Hoffman et al., in The Pharmacological Basis of Therapeutics, Gilman, et al., eds., Pergamon Press, New York, 1990, 8th edition, Chapter 10, pp. 187-220.

Adrenergic receptor antagonists include the subclasses of alpha-adrenergic receptor antagonists and beta-adrenergic receptor antagonists. Suitable examples of neurologically active agents that can be classified as alpha-adrenergic receptor antagonists include, but are not limited to, phenoxybenzamine and related haloalkylamines, phentolamine, tolazoline, prazosin and related drugs, ergot alkaloids and the like. Either selective or nonselective beta-adrenergic receptor antagonists are suitable for use in the present invention, as are other miscellaneous beta-adrenergic receptor antagonists. See Hoffman et al., in The Pharmacological Basis of Therapeutics, Gilman, et al., eds., Pergamon Press, New York, 1990, 8th edition, Chapter 11, pp. 221-243.

Antimuscarinic drugs are exemplified by the group consisting of atropine, scopolamine, homatropine, belladonna, methscopolamine, methantheline, propantheline, ipratropium, cyclopentolate, tropicamide, pirenzepine and the like. See Brown, J. H., in The Pharmacological Basis of Therapeutics, Gilman, et al., eds., Pergamon Press, New York, 1990, 8th edition, Chapter 8, pp. 150-165.

In addition, therapeutic agents that act at the neuromuscular junction and autonomic ganglia are contemplated by the invention. Suitable examples of such neurologically active agents that can be classified as agents that act at the neuromuscular junction and autonomic ganglia include, but are not limited to tubocurarine, alcuronium, beta-Erythroidine, pancuronium, gallamine, atracurium, decamethonium, succinylcholine, nicotine, labeline, tetramethylammonium, 1,1-dimethyl-4-phenylpiperazinium, hexamethonium, pentolinium, trimethaphan and mecamylamine, and the like. See Taylor, P., in The Pharmacological Basis of Therapeutics, Gilman, et al., eds., Pergamon Press, New York, 1990, 8th edition, Chapter 8, pp. 166-186.

The invention also contemplates the administration of drugs acting on the central nervous system and the peripheral nervous system. Such neurologically active agents can include nonpeptide neurotransmitters, peptide neurotransmitters and neurohormones, proteins associated with membranes of synaptic vessels, neuromodulators, neuromediators, sedative-hypnotics, antiepileptic therapeutic agents, therapeutic agents effective in the treatment of Parkinsonism and other movement disorders, opioid analgesics and antagonists and antipsychotic compounds.

Nonpeptide neurotransmitters include the subclasses of neutral amino acids—such as glycine and gamma-aminobutyric acid and acidic amino acids—such as glutamate, aspartate, and NMDA receptor antagonist-MK801 (Dizocilpine Maleate). L. L. Iversen, Neurotransmissions, Research biochemicals International, Vol. X, no. 1, February 1994. Other suitable nonpeptide neurotransmitters are exemplified by acetylcholine and the subclass of monoamines—such as dopamine, norepinephrine, 5-hydroxytryptamine, histamine, and epinephrine.

Neurotransmitters and neurohormones that are neuroactive peptides include the subclasses of hypothalamic-releasing hormones, neurohypophyseal hormones, pituitary peptides, invertebrate peptides, gastrointestinal peptides, those peptides found in the heart—such as atrial naturetic peptide, and other neuroactive peptides. See J. H. Schwartz, "Chemical Messengers: Small Molecules and Peptides" in Principles of Neural Science, 3rd Edition; E. R. Kandel et al., Eds.; Elsevier: New York; Chapter 14, pp. 213-224 (1991).

The subclass of hypothalamic releasing hormones includes as suitable examples, thyrotropin-releasing hormones, gonadotropin-releasing hormone, somatostatins, corticotropin-releasing hormone and growth hormone-releasing hormone.

The subclass of neurohypophyseal hormones is exemplified by agents such as vasopressin, oxytocin, and neurophysins. Likewise the subclass of pituitary peptides is exemplified by the group consisting of adrenocorticotropic hormone, beta-endorphin, alpha-melanocyte-stimulating hormone, prolactin, luteinizing hormone, growth hormone, and thyrotropin.

Suitable invertebrate peptides are exemplified by the group comprising FMRF amide, hydra head activator, proctolin, small cardiac peptides, myomodulins, buccolins, egg-laying hormone and bag cell peptides. The subclass of gastrointestinal peptides includes such therapeutic agents as vasoactive intestinal peptide, cholecystokinin, gastrin, neurotensin, methionine-enkephalin, leucine-enkephalin, insulin and insulin-like growth factors I and II, glucagon, peptide histidine isoleucineamide, bombesin, motilin and secretins.

Suitable examples of other neuroactive peptides include angiotensin II, bradykinin, dynorphin, opiocortins, sleep peptide(s), calcitonin, CGRP (calcitonin gene-related peptide), neuropeptide Y, neuropeptide Yy, galanin, substance K (neurokinin), physalaemin, Kassinin, uperolein, eledoisin and atrial naturetic peptide.

Proteins associated with membranes of synaptic vesicles include the subclasses of calcium-binding proteins and other synaptic vesicle proteins.

The subclass of calcium-binding proteins further includes the cytoskeleton-associated proteins—such as caldesmon, annexins, calelectrin (mammalian), calelectrin (torpedo), calpactin I, calpactin complex, calpactin II, endonexin I, endonexin II, protein II, synexin I; and enzyme modulators.

Other synaptic vesicle proteins include inhibitors of mobilization (such as synapsin Ia,b and synapsin IIa,b), possible fusion proteins such as synaptophysin, and proteins of unknown function such as p29, VAMP-1,2 (synaptobrevin), VAT-1, rab 3A, and rab 3B. See J. H. Schwartz, "Synaptic Vessicles" in Principles of Neural Science, 3rd Edition; E. R. Kandel et al., Eds.; Elsevier: New York; Chapter 15, pp. 225-234 (1991).

Neuromodulators can be exemplified by the group consisting of $CO_2$ and ammonia (E. Flory, Fed. Proc., 26, 1164-1176 (1967)), steroids and steroid hormones (C. L. Coascogne et al., Science, 237, 1212-1215 (1987)), adenosine and other purines, and prostaglandins.

Neuromediators can be exemplified by the group consisting of cyclic AMP, cyclic GMP (F. E. Bloom, Rev. Physiol. Biochem. Pharmacol., 74, 1-103 (1975), and cyclic nucleotide-dependent protein phosphorylation reactions (P. Greengard, Distinguished Lecture Series of the Society of General Physiologists, 1, Raven Press: New York (1978)).

Sedative-hypnotics can be exemplified by the group consisting of benzodiazepines and buspirone, barbiturates, and miscellaneous sedative-hypnotics. A. J. Trevor and W. L. Way, "Sedative-Hypnotics" in Basic and Clinical Pharmacology; B. G. Katzung, Ed.; Appleton and Lange; Chapter 21, pp. 306-319 (1992).

Suitable antiepileptic drugs can be exemplified by the groups consisting of, but not limited to, hydantoins such as phenytoin, mephenytoin, and ethotoin; anticonvulsant barbiturates such as phenobarbital and mephobarbital; deoxybarbiturates such as primidone; iminostilbenes such as carbamazepine; succinimides such as ethosuximide, methsuximide, and phensuximide; valproic acid; oxazolidinediones such as trimethadione and paramethadione; benzodiazepines and other antiepileptic agents such as phenacemide, acetazolamide, and progabide. See T. W. Rall et al., "Drugs Effective in the Therapy of the Epilepsies", in The Pharmacological Basis of Therapeutics, 8th Edition; A. G. Gilman et al., Eds.; Pergamon Press: New York; Chapter 19, pp. 436-462 (1990).

Neurologically active agents that are effective in the treatment of Parkinsonism and other movement disorders include, but are not limited to, dopamine, levodopa, carbidopa, amantadine, baclofen, diazepam, dantrolene, dopaminergic agonists such as apomorphine, ergolines such as bromocriptine, pergolide, and lisuride, and anticholinergic drugs such as benztropine mesylate, trihexyphenidyl hydrochloride, procyclidine hydrochloride, biperiden hydrochloride, ethopropazine hydrochloride, and diphenhydramine hydrochloride. See J. M. Cedarbaum et al., "Drugs for Parkinson's Disease, Spasticity, and Acute Muscle Spasms", in The Pharmacological Basis of Therapeutics, 8th Edition; A. G. Gilman et al., Eds.; Pergamon Press: New York; Chapter 20, pp. 463-484 (1990).

Suitable opioid analgesics and antagonists can be exemplified by the group consisting of, but not limited to, endogenous opioid peptides such as enkephalins, endorphins, and dynorphins; morphine and related opioids such as levorphanol and congeners; meperidine and congeners such as piperidine, phenylpiperidine, diphenoxylate, loperamide, and fentanyl; methadone and congeners such as methadone and propoxyphene; pentazocine; nalbuphine; butorphanol; buprenorphine; meptazinol; opioid antagonists such as naloxone hydrochloride; and centrally active antitussive agents such as dextromethorphan. See J. H. Jaffe et al., "Opioid Analgesics and Antagonists" in The Pharmacological Basis of Therapeutics, 8th Edition; A. G. Gilman et al., Eds.; Pergamon Press: New York; Chapter 21, pp. 485-521 (1990).

Neurologically active agents that can be used to treat depression, anxiety or psychosis are also useful in the present conjugate. Suitable antipsychotic compounds include, but are not limited to, phenothiazines, thioxanthenes, dibenzodiazepines, butyrophenones, diphenylbutylpiperidines, indolones, and rauwolfia alkaloids. Mood alteration drugs that are suitable for use in the present invention include, but are not limited to, tricyclic antidepressants (which include tertiary amines and secondary amines), atypical antidepressants, and monoamine oxidase inhibitors. Examples of suitable drugs that are used in the treatment of anxiety include, but are not limited to, benzodiazepines. R. J. Baldessarini, "Drugs and the Treatment of Psychiatric Disorders", in The Pharmacological Basis of Therapeutics, 8th Edition; A. G. Gilman et al., Eds.; Pergamon Press: New York; Chapter 18, pp. 383-435 (1990).

The neurologically active agent useful in the present conjugate may also be a neuroactive protein, such as human and chimeric mouse/human monoclonal antibodies, erythropoietin and G-CSF, orthoclone OKT3, interferon-gamma, interleukin-1 receptors, t-PA (tissue-type plasminogen activator), recombinant streptokinase, superoxide dismutase, tissue factor pathway inhibitor (TFPI). See Therapeutic Proteins: Pharmacokinetics and Pharmacodynamics; A. H. C. Kung et al., Eds.; W. H. Freeman: New York, pp 1-349 (1993).

The neurologically active agent useful in the present conjugate may also be a neuroactive nonprotein drug, such as neurotransmitter receptors and pharmacological targets in Alzheimer's disease; Design and Synthesis of BMY21502: A Potential Memory and Cognition Enhancing Agent; muscarinic agonists for the central nervous system; serotonic receptors, agents, and actions; thiazole-containing 5-hydroxytryptamine-3 receptor antagonists; acidic amino acids as probes of glutamate receptors and transporters; L-2-(carboxycyclopropyl)glycines; and N-Methyl-D-aspartic acid receptor antagonists. See Drug Design for Neuroscience; A. P. Kozikowski, Ed.; Raven Press: New York, pp 1-469 (1993).

The neurologically active agent useful in the present invention may also be an approved biotechnology drug or a biotechnology drug in development. Exemplary members of this group are included on Tables 1 and 2 of U.S. Pat. No. 5,604,198 (approved biotechnology drugs and biotechnology drugs in development, respectively) and may be found in J. E. Talmadge, Advanced Drug Delivery Reviews, 10, 247-299 (1993), each of which are incorporated by reference.

The invention also contemplates administration of cancer therapies through the BBBD. Non-limiting examples of anti-cancer agents and drugs that can be used in combination with one or more compositions and methods of the invention for the treatment of cancer include, but are not limited to, one or more of: 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

Other examples of agents useful in the treatment of cancer include, but are not limited to, one or more of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Therapeutic Antibodies

The method of the invention specifically contemplates the enhanced ability to deliver therapeutic antibodies in a targeted manner across the BBB. The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of protein antigen of interest. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of a protein antigen of interest.

The preparation of monoclonal antibodies is well known in the art; see for example, Harlow et al., Antibodies: A Laboratory Manual, page 726 (Cold Spring Harbor Pub. 1988). Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to a target disease peptide in the brain or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352:624-628; Gram et al. (1992) PNAS 89:3576-3580.

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Fully human antibodies are also contemplated. Fully humanized antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol. 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology, 10:779-783 (1992)); Lonberg et al. (Nature, 368:856-859 (1994)); Morrison (Nature, 368: 812-13 (1994)); Fishwild et al, (Nature Biotechnology, 14:845-51 (1996)); Neuberger (Nature Biotechnology, 14:826 (1996)); and Lonberg and Huszar (Intern. Rev. Immunol., 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., Science 246:1275-1281 (1989)) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. Similar procedures are disclosed in WO 93/08829, published May 13, 1993, and Traunecker et al., EMBO J., 10:3655-3659 (1991).

Antibody variable domains with the desired binding specificities (antibody-antigen combining sites) can be fused to immunoglobulin constant domain sequences. For further details of generating bispecific antibodies see, for example, Suresh et al., Methods in Enzymology, 121:210 (1986); and Brennan et al., Science 229:81 (1985).

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The "diabody" technology described by Hollinger et al., Proc. Natl. Acad. Sci. USA 90:6444-6448 (1993) has provided an alternative mechanism for making bispecific antibody fragments. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991). Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond.

Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a chemical agent, or a radioactive isotope (i.e., a radioconjugate) for administration to the brain using the methods of the invention. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide-interchange reaction.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight. Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

Formulations

Preparations for administration of a therapeutic of the invention include sterile aqueous or non-aqueous solutions, suspensions, and emulsions, and in particular, formulations suitable for intraarticular infusion or injection via a catheter. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The compounds, nucleic acid molecules, polypeptides, and antibodies (also referred to herein as "therapeutic agents") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration, and by intraarterial infusion via a catheter. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration (e.g., via a catheter system), suitable carriers include physiological saline, bacteriostatic water, Cremophor (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethan-e, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

System for Modeling Optimized BBB Opening

In another aspect, the present invention provides a computer-implemented system for measuring, monitoring, processing, and calculating a model for optimized BBB opening in a subject under going BBB hyperosmoral-based perfusion during real-time MRI imaging. The computer-implemented system comprises a processor that calculates a model for optimized BBB opening in a subject that is based on user-defined input data (e.g., perfusion flow rate, hyperosmolar agent concentration, perfusion time, catheter tip position, patient data (e.g., age, family history, medical record, etc.) together with MRI based visual input data (e.g., measurements of the size or extent of brain parenchymal flow and/or BBB opening measurements taken in real-time during perfusion). Additional data, such as the level or concentration of a marker agent (e.g., fluorescent compound, drug analog) that has crossed the open BBB region, may also be provided to the processing device. The processing devices receives the user input data and the MRI-based data and processes same via a suitable algorithm or software and calculates a model that predicts the optimal conditions for BBB opening in the subject. The processed information and/or model may be stored in a storage device or a database.

In a further aspect, the present invention relates to the use of the predictive models of the invention to predict the optimal conditions for BBB opening that may be used on a new subject without having to first establish optimal BBB conditions in said patient, i.e., avoid having to empirically test multiple sets of conditions to identify the most suitable BBB formation conditions.

Figure 2:
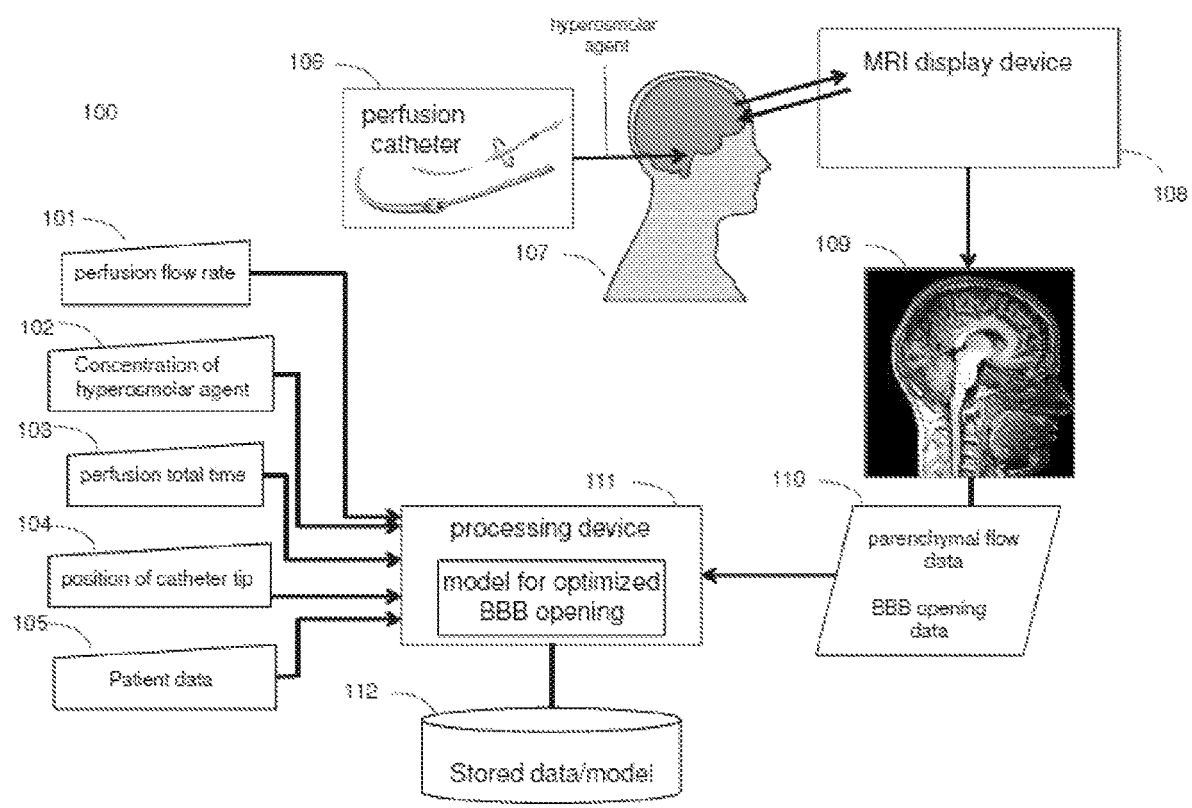
FIG. 2. Provides a schematic block diagram of an exemplary embodiment of a computer-implemented catheter-based system of the invention for measuring, monitoring, processing, and calculating a model for optimized BBB opening in a subject using MRI real-time measurements during perfusion of hyperosmolar agent.

One embodiment of this aspect of the invention is reflected in FIG. 2, which depicts a schematic block diagram of a computer-implemented system 100 of the invention for measuring, monitoring, processing, and calculating a model for optimized BBB opening in a subject under going BBB hyperosmolar-based perfusion during real-time MRI imaging. The method involves perfusion catheter 106 which is used to administer intraarterially a hyperosmolar agent (e.g., mannitol) to a patient. Parameters such as agent concentration, flow rate, time, and catheter position may be adjusted in real-time during MR imaging (which is preceeded by an administration of an MRI contrast agent) (not shown). The MR imaging (display device 108) produces real-time visual data/information 109/110, which can include, for example, the images per se, but also parenchymal flow data (e.g., physical area of detected/visible parenchymal flow into the brain parenchym) and BBB opening data (e.g., to extend area of opening is detectable and measurable). This information flows to the processing device 111. In addition, the user manually provides (or they system is configured to automatically provide in some cases via sensors and electronics, etc.) parameters such as perfusion flow rate 101, concentration of the agent 102, perfusion total time 103, catheter tip position 104, and patient data 105 (e.g., patient health and medical history, weight, diet, smoking history, etc.) to the processing device. The processing device 111 then calculates a model for optimized BBB opening in the patient, which can be stored in a database 112. Database 112 and predictive model can then be used to predict the optimal conditions (e.g., perfusion flow rate 101, concentration of the agent 102, perfusion total time 103, catheter tip position 104) that can be used in connection with a new patient, thereby avoiding or mitigating the amount of perfusion titration that must be done on the subject prior to drug delivery.

Once the optimal conditions are either measured or modeled, the BBB can be opened, followed by the administration of a desired therapeutic agent delivered locally and proximal to the BBB opening, thereby maximizing drug delivery to the brain.

This invention is further illustrated by the following examples which should not be construed as limiting. The contents of all references and published patents and patent applications cited throughout the application are hereby incorporated by reference.

EXAMPLES

This invention is further illustrated by the following examples which should not be construed as limiting. Those skilled in the art will recognize that the invention may be practiced with variations on the disclosed structures, materials, compositions and methods, and such variations are regarded as within the ambit of the invention.

Example 1: Highly Selective MRI-Guided Targeting of Chemotherapy to the Brainstem Across a Focally Disrupted Blood Brain Barrier in a Rabbit Model Purpose Inadequate penetration of chemotherapeutic agents across an intact blood brain barrier (BBB) and lack of methodology for precise drug delivery represents a major therapeutic challenge in the treatment of pontine gliomas. The purpose of this study was to demonstrate that intra-arterial (IA) chemotherapy administration could be performed with high precision after focal blood brain barrier disruption (BBBD) and that parenchymal penetration of drug-sized molecules could be validated with fluorescent microscopy.

Materials and Methods

IACUC approved this protocol. Using a hybrid MRI angiography suite (Miyabi, Siemens), the left vertebral artery of 4-kg New Zealand white rabbits was catheterized with a 4-French catheter. A 1.7-French microcatheter was then advanced into the basilar artery. The rabbits were transported to a 3T MRI (Magnetom Trio, Siemens) for anatomical reference images (horizontal and sagittal T2-weighted (TR/TE=1500/105)). Real-time assessment of trans-catheter contrast enhanced perfusion territory using GE-EPI sequence (TR/TE=3000/30; 60 measurements) was performed during infusion of iron oxide nanoparticle solution (Feraheme) (rates of 0.001-0.1 ul/s).

IA mannitol (25% over 5 minutes at the pre-determined optimized infusion rate) was administered for focal BBBD. Intravenous gadolinium (Magnevist, 0.5 mM, 0.125 mmol/kg) was administered followed by T1-weighted (TR/TE=300/9.1) images. IA fluorescein isothiocyanate (FITC) (19 μmol), a surrogate marker for the chemotherapy drug melphalan, was then infused. The brains were immediately harvested and snap frozen on crushed dry ice. Cryo-sectioned tissue slices were counterstained with DAPI and imaged by fluorescence microscopy (Zeiss) for detection of extravasated fluorescein.

The drug (melphalan) was conjugated to a fluorescent moiety (fluorescein) to obtain a melphalan-fluorescein conjugate, for subsequent studies of direct monitoring of this drug across the BBB. The conjugate was then purified using silica-gel columns and characterized by HPLC, NMR, and MS.

Results

Feraheme-enhanced real-time MRI demonstrated an optimal injection rate of 0.01 ml/sec to selectively perfuse the pons. Using this rate, IA mannitol resulted in specific pontine BBBD as visualized by gadolinium enhanced T1-weighted images. Postmortem evaluation of fluorescein distribution correlated well with T1 enhancement.

Figure 3:
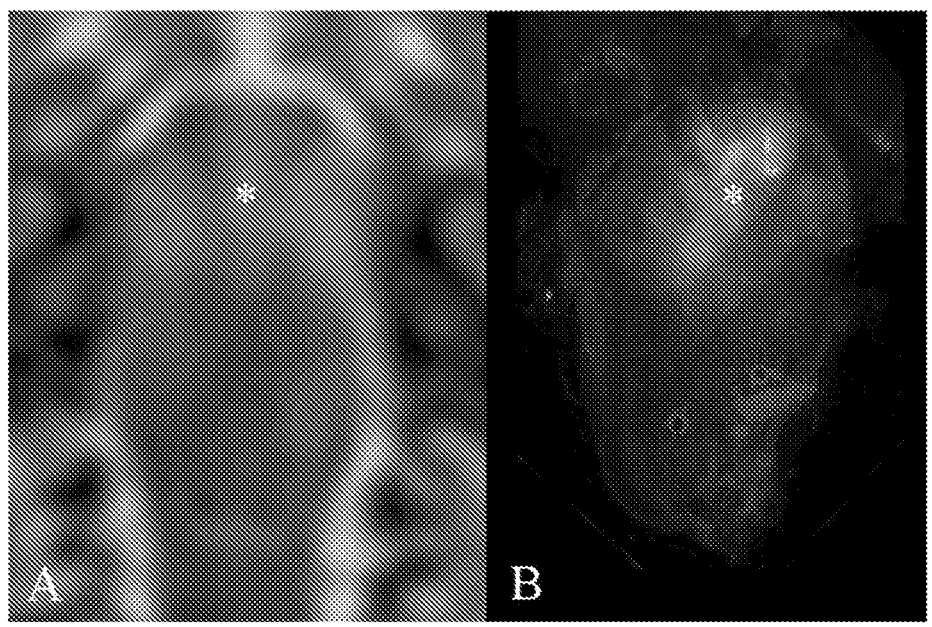
FIG. 3. Provides the results of Example 1. Horizontal post gadolinium T1-weighted image (A) and histological preparation of a brain slice through the pons and medulla demonstrate pontine enhancement (asterisk) and pontine uptake of FITC (green) with nuclear DAPI counterstain (blue).

As shown in FIG. 3, horizontal post gadolinium T1-weighted image (FIG. 3A) and histological preparation of a brain slice through the pons and medulla demonstrated pontine enhancement (asterisk) and pontine uptake of FITC (shading immediately around asterisk of FIG. 3B) with nuclear DAPI counterstain (radial shading around asterisk of FIG. 3B).

Conclusions:

MRI-guided targeted IA mannitol-induced BBBD in rabbit brainstems could be performed, allowing for highly selective delivery of chemotherapeutic agents to the pons. Assessment of therapeutic drug delivery after BBBD could be depicted with fluorescent agents.

Example 2: Intra-Arterial Mannitol-Induced Blood Brain Barrier Disruption in a Rabbit Model The transfemoral approach for IA mannitol-induced BBBO of the vertebrobasilar system in a rabbit model was demonstrated to be feasible and reproducible.

Anesthesia and Animal Preparation

The Institutional Animal Care and Use Committee approved this protocol. Eight 4-kg New Zealand white rabbits were sedated with intramuscular Acepromazine (1 mg/kg) and Ketamine Hydrochloride (20 mg/kg), after which intravenous access was established through a marginal ear vein. Intravenous Propofol (6.44 mg/kg) was then administered to facilitate endotracheal intubation and the rabbits were maintained on 2% Isoflurane gas. A 4-French sheath was surgically placed in the right femoral artery. Oxygen saturations and respiratory rates were monitored.

Digital Subtraction Angiography

Via a transfemoral approach, a 4-French Glide catheter (Terumo, Somerset, N.J.) was advanced over a 0.035-inch wire and the left vertebral artery was selectively catheterized. Under roadmap guidance, a 1.7-French Prowler 10 microcatheter (Codman Neuro, Raynham, M A) was advanced over a 0.014-inch microwire into the V4 segment (four rabbits) or basilar artery (four rabbits). Microcatheter angiography was performed to confirm position and assess antegrade flow. The catheters were secured in place and maintained on heparinized saline flush (4000 IU heparin/1 L normal saline).

Interventional MRI Technique

The rabbits were transported to a 3T MRI (Magnetom Trio, Siemens) and underwent baseline T2 (TR/TE 1500/105) and T1 (TR/TE 300/9.1) weighted images of the brain. The horizontal plane best displayed the brainstem in its entirety and was chosen as the working view for dynamic susceptibility contrast (DSC) enhanced trans-catheter perfusion. IA Feraheme (dissolved in saline at 1:100; 0.3 mgFe/ml) was infused between 0.001 ml/sec to 0.1 ml/sec for 30 seconds to assess trans-catheter parenchymal perfusion territory at specific speeds. For controlled contrast agent and drug administration, a standard infusion pump (Harvard apparatus) was utilized.

Real-time GE-EPI images (TE=36 ms, TR=3000 ms, FOV=1080, matrix=128, and temporal resolution=3 s.) were obtained for DSC. Immediately after the Feraheme injection, 25% warmed IA mannitol was administered at the optimal rate previously determined by the Feraheme injection. The duration of the mannitol infusion was determined by the infusion speed. Five minutes after IA mannitol, 1.5 ml of gadolinium (Magnevist, 0.125 mmol/kg) and Evans Blue (EB) 2% (2 mg/kg) were injected intravenously. T1-weighted images were acquired post gadolinium.

To demonstrate the role of microcatheter tip placement, the microcatheter was withdrawn more proximally within basilar artery inside the MR scanner, after which the Feraheme and mannitol infusions were repeated. Osirix (Pixmeo) and Amira (FEI) software were used for image processing and visualization.

Correlation of Perfusion Territory and the BBBO Area:

DSC Feraheme MR images delineated the region of trans-catheter perfusion territory and T1-weighted gadolinium enhanced MR images depicted the region of BBBO. Slice selection was based on the greatest territory of BBBO. Identical slice geometry for T1 and DSC scans facilitated spatial co-registration of the regions of interest and calculation of the surface areas ($cm^2$) of the perfusion territory, BBBO, mismatch areas, and the total brain area of the analyzed slice.

Figure 4:
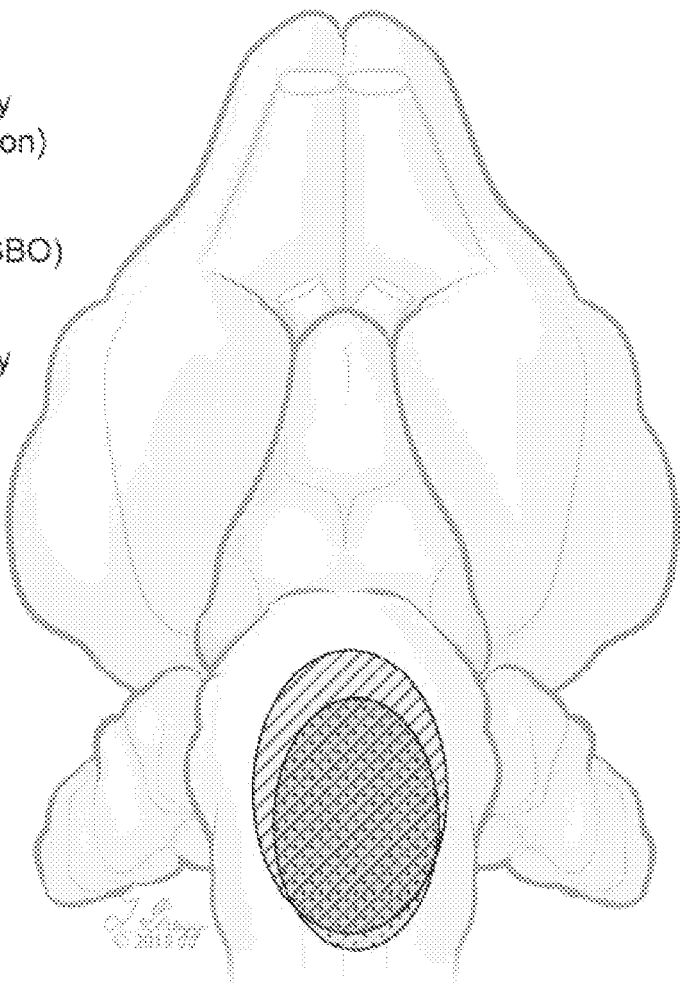
FIG. 4. Provides an artistic rendering showing evaluation of the iron oxide infusion as a predictor of the BBBO territory. Horizontal view of the rabbit brain shows the 4 brain regions that were segmented and measured for assessment of BBBO accuracy. The patterned regions depict the MRI imaging findings from DSC and T1 post-gadolinium weighted sequences. The shaded areas show statistical results.

Accuracy of BBBO Procedure:

For evaluation of the iron oxide infusion as a predictor of the BBBO territory, the area ($cm^2$) for 4 brain regions was segmented and the following were measured (FIG. 4): 1). The overlapping area for both T1 enhancement and DSC MRI hypointensity=true positive (TP); 2) The hypointense area which did not overlap with T1 enhancement=false positive (FP); 3) The area of T1 enhancement which was not hypointense on DSC MRI=false negative (FN); 4) The area of the brain with no signal changes on T1 or T2=true negative (TN).

Post Mortem Analysis

The rabbits were perfused with 4% paraformaldehyde solution. The brains were harvested and coronal 1-mm slices were obtained using a brain matrix. The BBBO territory was assessed by EB extravasation.

Statistics:

The mean values from 7 rabbits for each of the 4 territories were extracted and were used for further calculations. One rabbit was excluded from calculations due to significant motion artifact, which degraded image quality. Standard validity analysis was performed and the positive predictive value was calculated: PPV=TP/(TP+FP), negative predictive value: NPV=TN/(TN+FN), sensitivity=TP/(TP+FN) and specificity=TN/(FP+TN) for prediction of the BBBO area (T1-weighted) using iron oxide infusion (T2-weighted).

Results

Feasibility of IA Trans Femoral Catheter-Based Approach to Access the Vertebro-Basilar Circulation in a Rabbit Model The rabbits' vertebral arteries were accessed via a transfemoral approach with clinically used 4-French catheters. The smaller caliber distal V4 segment and basilar artery were sufficiently large to accommodate a 1.7-French microcatheter and maintain antegrade flow. Positioning of the 4-French catheter and microcatheter within the rabbits' vertebrobasilar system was performed safely and efficiently using fluoroscopic guidance (data not shown).

Anatomic MR Imaging of the Rabbit Brain

The T2- and T1-weighted sequences provided diagnostic quality images of the brain without obscuration from the indwelling microcatheter. The horizontal and sagittal planes offered the optimal working views of the brainstem (data not shown).

Dynamic Susceptibility Contrast (DSC) Imaging for Assessment and Optimization of Transcatheter Perfusion Territory DSC MRI of IA Feraheme boluses allowed real-time assessment of local parenchymal perfusion, manifested as MRI signal reduction (hypointensity) (data not shown). Real-time DSC MRI depicted distinct areas of parenchymal perfusion, whereas conventional x-ray DSA showed perfused vasculature. Rapid Feraheme washout with clearance of the hypointensities immediately after the bolus allowed for repetitive boluses at different speeds and microcatheter locations with subsequent DSC imaging; thus these parameters could be adjusted to achieve the desired perfusion territory. The dynamically acquired temporal changes in image intensity facilitated image post-processing. Subtraction perfusion images could be created and overlaid with higher resolution anatomical T2 images to provide a better appreciation of the local perfusion territory and more precise anatomical location (FIG. 5B-5D, 5I-5K). The rate of injection affected the perfusion area with slower rates producing a smaller, localized region and faster speeds resulting in a larger, more diffuse territory (FIG. 3 A-D). Notably, a given injection rate resulted in different ranges of perfusion territories in different rabbits, necessitating titration of injection speed to achieve the targeted area for each rabbit.

The microcatheter tip position in the vertebro-basilar circulation also affected the perfusion area with distribution to the medulla, cervical spinal cord, and adjacent paraspinal muscles when in the V4 segment (FIG. 5H-5K), whereas a position in the mid basilar artery resulted in supply to the pons, medulla and cerebellum (FIG. 5A-5D).

Figure 6A:
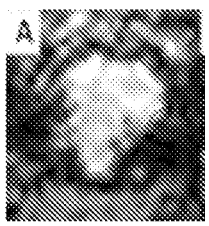
FIGS. 6A to 6G. Provide MRI and angiographic images demonstrating the role of infusion rate and microcatheter tip position. DSC MR images before (FIGS. 6A, 6C) and during (FIGS. 6B, 6D) IA Feraheme infusions at slow (FIGS. 6A, 6B) and fast (FIGS. 6C, 6D) rates demonstrated a larger perfusion territory with the faster infusion rate. Perfusion territory was also affected by small changes in microcatheter position even within the same vascular territory. Frontal angiographic view showed a microcatheter in the mid-basilar artery (top arrow), which was subsequently withdrawn more proximally (bottom arrow). The two positions correspond to differential trans-catheter perfusion territories, with FIG. 6F corresponding to the top arrow and FIG. 6G corresponding to the bottom arrow.
Figure 6B:
Figure 6C:
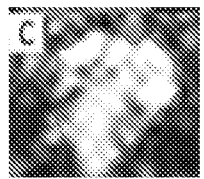
Figure 6D:
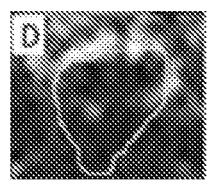
Figure 6E:
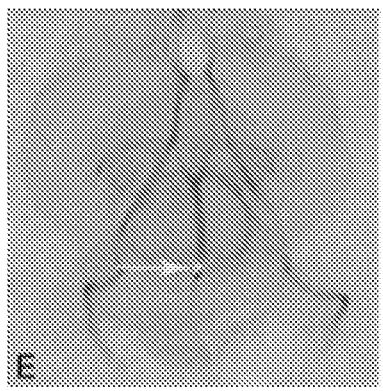
Figure 6F:
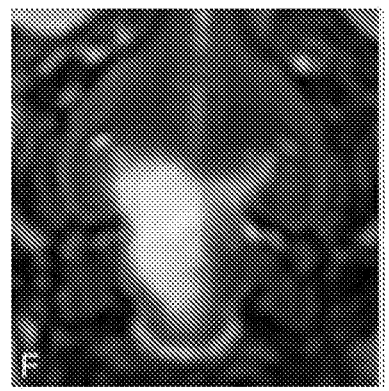
Figure 6G:

These territories reflected the expected anatomic arterial supply from small branches arising from the V4 segment and the basilar artery, respectively. Importantly, even small changes in the microcatheter tip position within the basilar artery resulted in differential perfusion of the brainstem based on the tortuosity and direction of flow within the basilar artery (FIG. 6E-6G).

Application of Transcatheter DSC Imaging and IA Mannitol for Precise, Transient, and Local BBBO:

Rate of IA Mannitol Infusion

BBBO also depended on the rate of IA mannitol infusion. IA mannitol was infused as bolus injections, ranging from 0.001 ml/sec to 0.26 ml/sec for 30 seconds, as well as continuous infusions from 0.001 ml/sec to 0.1 ml/sec for up to 15 minutes. The 0.001 ml/sec rate of infusion did not produce BBBO, neither as a bolus injection nor when administered as a slow, continuous infusion for up to 15 minutes. BBBO was produced with IA mannitol delivered at rates of at least 0.01 ml/sec. Slower rates of IA mannitol were more localized and better tolerated as irreversible respiratory depression and BBBO in the right PCA territory in addition to brainstem BBBO was present when IA mannitol was infused at 0.26 ml/sec for 30 seconds. No other infusion rates resulted in supratentorial BBBO. Safe and optimal infusion rates were between 0.005-0.05 ml/sec×30 seconds, which produced localized BBBO without respiratory depression (FIG. 5).

Figure 5A:
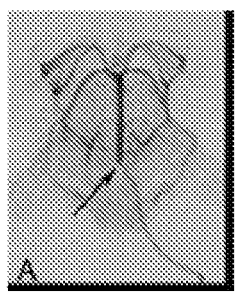
FIGS. 5A to 5N. Show the focal blood brain barrier opening (BBBO) predicted by intra-arterial injections. Microcatheter placement in the mid basilar artery (FIG. 5A) and V4 segment (FIG. 5H) are shown. The DSC MRI before (FIGS. 5B, 5I) and during IA Feraheme injections (FIGS. 5C, 5J) demonstrated signal intensity loss (asterisks) and the area of transcatheter perfusion was visualized on colorcoded (shaded) subtraction images overlaid on the T2 scan (FIGS. 5D, 5K). Gadolinium enhanced T1-weighted images before (FIGS. 5E, 5L) and after (FIGS. 5F, 5M) intraarterial mannitol injection demonstrated focal BBBO in the pons, cerebellum (FIG. 5F) and medulla (FIG. 5M), respectively. These areas correspond with Evans Blue extravasation (shaded, FIGS. 5G, 5N).
Figure 5B:
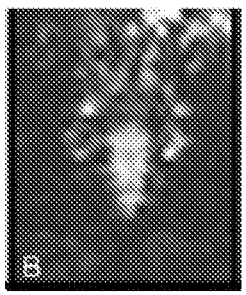
Figure 5C:
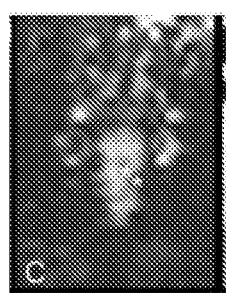
Figure 5D:
Figure 5E:
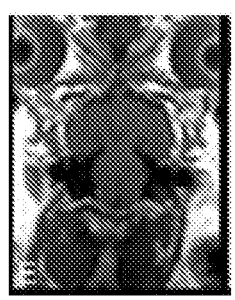
Figure 5F:
Figure 5G:
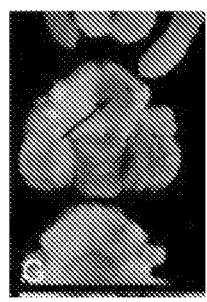
Figure 5H:
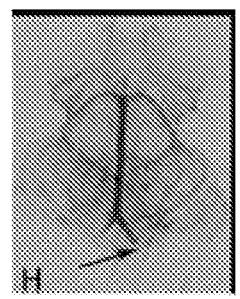
Figure 5I:
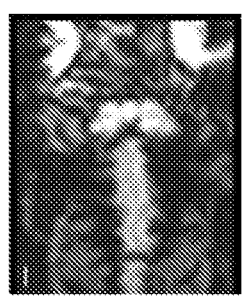
Figure 5J:
Figure 5K:
Figure 5L:
Figure 5M:
Figure 5N:
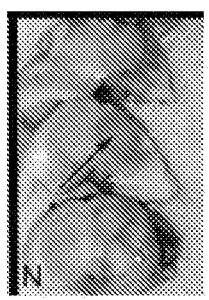

Location of Microcatheter for IA Mannitol Infusion:

Microcatheter position had substantial effect on focal BBBO, which was predicted by the DSC imaging of IA Feraheme. BBBO was localized to the medulla for catheters placed in the V4 segment whereas microcatheters in the mid basilar artery created BBBO in the pons, medulla, and cerebellum (FIG. 5N, 5G).

BBBO Using IA Injection of Mannitol was Transient and without Permanent Damage

One randomly selected rabbit was allowed to survive for one day after BBBO to assess for neurologic or MRI sequelae of BBBO. The microcatheter was placed in the mid basilar artery and localized BBBO, manifested as focal gadolinium enhancement, was evident in the pons. MR images after gadolinium the next day showed neither enhancement nor signal abnormalities on the T2-weighted images. EB was administered and no EB extravasation was present on postmortem brain slices (data not shown).

The DSC images with IA Feraheme were predictive of the BBBO area, which correlated with subsequent MRI enhancement and Evans Blue (EB) extravasation (FIG. 5).

Validation of Procedure

It was discovered that PPV=69.65%, NPV=96.73%, sensitivity=87.13% and specificity=90.94%. This suggested that by using transcatheter infusion of iron oxide and DSC MRI, it was possible to predict at almost 70% certainty, the exact location of BBBO and it was also possible to predict at above 95% certainty where the BBB would remain intact. This method was further characterized by remarkably high sensitivity=87%, and specificity 91%.

Thus, a satisfactory PPV near 70% was achieved. This indicated that the application of this method to intra-arterial tumor targeting, when the perfusion area is optimized to cover the entire tumor territory, could enable 70% BBBO in the tumor area. This allows for more efficacious drug delivery via higher concentrations and greater drug penetration. This method also enhances the safety profile of the intervention as the NPV value of 95% signified that only 5% of BBBO would occur outside the area indicated by the iron oxide infusion, limiting unintentional drug exposure of healthy parenchyma to 5%.

Without wishing to be bound by theory, the larger territory highlighted on DSC MRI compared with the area of T1 enhancement was likely a result of blooming effect, which is common for susceptibility agents such as iron oxide. This artifact can likely be reduced by further optimization of pulse sequence or/and lowering the concentration of iron oxide. Increases in PPV, while maintaining optimal NPV, are obtained by such methods.

This work has shown that IA mannitol-induced focal BBBO is viable as a predictable and highly controlled procedure that can be targeted to specific regions and validated by realtime non-invasive MRI methods. These features address and reduce the major limitations of the osmotic BBBO technique. The IA route for BBBO also offers a great advantage by enabling and enhancing subsequent IA drug delivery during the same procedure.

The safety of BBBO by intra-arterial infusion of mannitol has been clinically established, however, this notion was also confirmed in the rabbit model by performing delayed MRI and histology in one rabbit. The absence of clinical and MRI abnormalities matched well with recognized clinical outcomes. MRI was essential not only for BBBO validation, but also for predicting and titrating both speed of injection and microcatheter tip position. The need to modify these parameters was evident in each animal, reflecting the flow dynamics within a specific vascular territory and each animal's individual hemodynamic variability. While microcatheter placement was performed using fluoroscopic guidance, the results presented herein emphasized the benefits of MRI and serve as an additional impetus towards developing neurointerventional MRI technology including catheter navigation under MRI guidance. Such approaches can streamline/adapt the described procedure with the added benefit of eliminating patient exposure to ionizing radiation. Indeed, there has been growing interest in this regard including MR-trackable catheters (13) and/or shape sensing technology (14). As the BBB is increasingly recognized as a major limitation to effective therapies for CNS tumors, innovative surgical and pharmacological strategies such as those described herein are required to circumvent it.

Accordingly, a transfemoral approach for IA mannitol-induced BBBO of the vertebrobasilar system in a rabbit model was demonstrated to be feasible and reproducible. Non-invasive real-time BBBO validation was demonstrated as accomplished with contrast-enhanced MRI. Furthermore, advanced MRI techniques, specifically DSC perfusion imaging, allowed for the dynamic depiction of transcatheter parenchymal flow, which enabled the prediction and titration of areas of BBBO.

Example 3: Intra-Arterial Mannitol-Induced Blood Brain Barrier Disruption in a Rabbit Model: Implications for Chemotherapeutic Drug Delivery in Brainstem Tumors Purpose One of the main challenges in brainstem tumor treatment is the poor penetration of chemotherapeutic drugs from the bloodstream across an intact blood brain barrier. The purpose of this study is to further demonstrate a rabbit model of mannitol-induced blood brain barrier disruption (BBBD).

Materials & Methods

This protocol was approved by the Institutional Animal Care and Use Committee. Four French sheaths were placed in the right femoral arteries of 4 kg New Zealand white rabbits. Using a hybrid MRI (magnetic resonance imaging) angiography suite (Miyabi, Siemens), a 4 French catheter was used to catheterize the left vertebral artery. Through the guide catheter, a 1.7 French microcatheter was advanced over a 0.014 inch microwire into the left V4 segment or basilar artery under roadmap guidance. All catheters were set to continuous heparinized saline flush. The rabbits were transported to a 3T (Magnetom Trio, Siemens) MRI for dynamic and post-mannitol injection images of the brain.

Coronal T2 (TE/TR=105/1500), T1 (TE/TR=9.1/300), and GE-EPI (TE/TR=30/3000; 60 measurements) images were obtained prior to intra-arterial (IA) mannitol injection. Dynamic EPI images were obtained during IA injection of feraheme (iron oxide nanoparticles, ~20 nm) (i.e., MRI contrast agent). IA mannitol (25%, 0.26 ml/sec for 30 seconds) was delivered in the left V4 segment. After 5 minutes, gadolinium (Magnevist) was injected intra-arterially (0.5 molar, 0.01 ml/sec for 1 minute), Evans blue s (EB) (2%, 2 ml/kg), known for rapid binding with albumins, was injected intravenously, and coronal T1 post-gadolinium images were acquired. The EB staining was evaluated post mortem on brain slices.

Results

Dynamic EPI depicted the perfusion territory following contrast agent injection via the vertebral or basilar artery. Manipulation of the injection rate resulted in differential brain parenchymal coverage. IA mannitol produced visible BBBD: diffuse bilateral enhancement of the brainstem, cerebellum and the PCA territory on gadolinium enhanced T1-weighted images. Necropsy revealed unilateral EB uptake within the brainstem notably smaller than the degree of T1 enhancement.

The data shows: A) Coronal post gadolinium T1-weighted image demonstrates diffuse bilateral enhancement of the brainstem. The unenhanced supratentorial brain is seen surrounding the brainstem. B) Selected rabbit brain slices show left sided EB extravasation in the brainstem.

A transfemoral approach for microcatheter IA mannitol delivery to the vertebrobasilar system in rabbits is feasible and produces BBBD. Assessment of BBBD for chemotherapy should consider the size of therapeutic agent, as differential extravasation across the BBB was seen with gadolinium versus EB.

REFERENCES

1. Kroll R A, Neuwelt E A. Outwitting the blood-brain barrier for therapeutic purposes: osmotic opening and other means. Neurosurgery 1998; 42:1083-99; discussion 99-100.
2. Budde M D, Janes L, Gold E, Turtzo L C, Frank J A. The contribution of gliosis to diffusion tensor anisotropy and tractography following traumatic brain injury: validation in the rat using Fourier analysis of stained tissue sections. Brain: a journal of neurology 2011; 134:2248-60.
3. Peschillo S, Miscusi M, Missori P. Endovascular superselective treatment of brain tumors: a new endovascular era? A quick review. Journal of neurointerventional surgery 2014.
4. Norbash A M B D, Marks M P. Techniques for reducing interventional neuroradiologic skin dose: tube position rotation and supplemental beam filtration. AJNR Am J Neuroradiol. 1996; 17(1):41-9. Epub 1996 Jan. 1.
5. Maeda M, Itoh S, Kimura H, Iwasaki T, Hayashi N, Yamamoto K, et al. Tumor vascularity in the brain: evaluation with dynamic susceptibility-contrast MR imaging. Radiology 1993; 189:233-8.
6. Neuwelt E A. Mechanisms of disease: the blood-brain barrier. Neurosurgery 2004; 54:131-40; discussion 41-2.
7. Rapoport S I. Effect of concentrated solutions on blood-brain barrier. The American journal of physiology 1970; 219:270-4.
8. Burkhardt J K, Riina H, Shin B J, Christos P, Kesavabhotla K, Hofstetter C P, et al. Intra-arterial delivery of bevacizumab after blood-brain barrier disruption for the treatment of recurrent glioblastoma: progression-free survival and overall survival. World Neurosurg 2012; 77:130-4.
9. Shin B J, Burkhardt J K, Riina H A, Boockvar J A. Superselective intra-arterial cerebral infusion of novel agents after blood-brain disruption for the treatment of recurrent glioblastoma multiforme: a technical case series. Neurosurgery clinics of North America 2012; 23:323-9, ix-x.
10. Yin D, Zhai Y, Gruber H E, Ibanez C E, Robbins J M, Kells A P, et al. Convection enhanced delivery improves distribution and efficacy of tumor-selective retroviral replicating vectors in a rodent brain tumor model. Cancer Gene Ther 2013; 20:336-41.
11. Yang X, Saito R, Nakamura T, Zhang R, Sonoda Y, Kumabe T, et al. Peritumoral leakage during intra-tumoral convection-enhanced delivery has implications for efficacy of peri-tumoral infusion before removal of tumor. Drug Deliv 2014:1-6.
12. Chai W Y, Chu P C, Tsai M Y, Lin Y C, Wang J J, Wei K C, et al. Magnetic resonance imaging for kinetic analysis of permeability changes during focused ultrasound-induced blood-brain barrier opening and brain drug delivery. J Control Release 2014; 192C:1-9.
13. Erturk M A, El-Sharkawy A M, Moore J, Bottomley P A. 7 Tesla MRI with a transmit/receive loopless antenna and B1-insensitive selective excitation. Magnetic resonance in medicine: official journal of the Society of Magnetic Resonance in Medicine/Society of Magnetic Resonance in Medicine 2014; 72:220-6.
14. Liu X, Iordachita, II, He X, Taylor R H, Kang J U. Miniature fiber-optic force sensor for vitreoretinal microsurgery based on low-coherence Fabry-Perot interferometry. Proceedings of SPIE 2013; 8218:821800.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A method of administering a therapeutic agent directly to the brain parenchyma through a compromised region of the blood-brain barrier in a subject having a brain disorder, comprising:
   disrupting the blood-brain barrier (BBB) at an isolated region by locally administering an effective amount of a hyperosmolar agent at said region using a catheter,
   locating an opening in the BBB using non-invasive MR (magnetic resonance) imaging with a contrast agent administered at said isolated region, and
   administering a therapeutically effective amount of a therapeutic agent at the located opening in the BBB.

2. The method of claim 1 wherein the brain disorder is a proliferative disorder.

3. The method of claim 1, wherein the brain disorder is a neurological disorder.

4. The method of claim 3, wherein the neurological disorder is brain damage, brain dysfunction, cranial nerve disorder, autonomic nervous system disorder, seizure disorder, movement disorder, sleep disorder, migraine, a central neuropathy, or a neuropsychiatric illness.

5. The method of claim 3, wherein the neurological disorder is Alzheimer's disease.

6. The method of claim 1, wherein the therapeutic agent is an agent for treating a proliferative disorder.

7. The method of claim 1, wherein the therapeutic agent is a small molecule pharmaceutical, a protein therapeutic, a therapeutic antibody, a therapeutic nucleic acid molecule, or a composition comprising any of the same.

8. The method of claim 1, wherein the disrupting of the BBB comprises adjusting an infusion rate of the hyperosmolar agent to control the opening in the BBB.

9. The method of claim 1, wherein the disrupting of the BBB comprises adjusting a length of time of perfusion of the hyperosmolar agent to control the opening in the BBB.

10. The method of claim 1, wherein the isolated region of the BBB is in the basilar artery.

11. The method of claim 1, wherein the contrast agent used to visual local parenchymal transcatheter perfusion is gadolinium and/or Feraheme or a combination thereof.

12. The method of claim 1, wherein the contrast agent is selected from the group consisting of: gadoterate (Dotarem); gadodiamide (Omniscan); gadobenate (MultiHance); gadopentetate (Magnevist, Magnegita, Gado-MRT ratiopharm); gadoteridol (ProHance); gadoversetamide (OptiMARK); gadoxetate (Primovist); gadobutrol (Gadovist); gadoterate (Dotarem); gadodiamide (Omniscan); gadobenate (MultiHance); gadopentetate (Magnevist); gadoteridol (ProHance); gadofosveset (Ablavar, formerly Vasovist); gadoversetamide (OptiMARK); gadoxetate (Eovist); and gadobutrol (Gadavist).

13. The method of claim 1, wherein the hyperosmolar agent is mannitol, glycerin, isosorbide, or urea.

14. The method of claim 1, wherein the disrupting of the BBB comprises administering the hyperosmolar agent at an optimized infusion rate that is based on user-defined input data and MR imaging data.

15. The method of claim 1 wherein the subject is a human.

16. A method of administering a therapeutic agent to the brain parenchyma through the blood-brain barrier in a human subject, comprising:
   selecting a potential opening of the blood-brain barrier by administering an effective amount of a hyperosmolar agent through an intraarterial catheter positioned at a region of the blood-brain barrier,
   locating an opening in the blood brain barrier using non-invasive magnetic resonance imaging with a contrast agent administered through the intraarterial catheter positioned at the region of the blood-brain barrier, and
   administering a therapeutically effective amount of a therapeutic agent through an intraarterial catheter positioned at the located, opening in the blood brain barrier.

17. The method of claim 16 wherein the subject is a human.

* * * * *